United States Patent [19]

Noujaim et al.

[11] Patent Number: 4,990,326

[45] Date of Patent: Feb. 5, 1991

[54] METHOD FOR DETECTING BLOOD PLATELETS

[75] Inventors: Antoine A. Noujaim, Sherwood Park; Bryan M. Longenecker, Edmonton, both of Canada

[73] Assignee: Summa Medical Corporation, Albuquerque, N. Mex.

[21] Appl. No.: 170,447

[22] Filed: Mar. 15, 1988

Related U.S. Application Data

[63] Continuation of Ser. No. 739,697, May 31, 1985, abandoned.

[51] Int. Cl.$^5$ .................. G01N 33/48; G01N 33/53; G01N 53/00; C12N 15/00
[52] U.S. Cl. .......................... 424/9; 424/85.8; 436/548; 530/387; 530/808; 530/809; 435/7.21; 435/172.2; 435/240.27; 435/7.32; 935/103; 935/107; 935/110
[58] Field of Search .................. 424/9, 85, 94.6; 436/173, 503, 504, 514, 548; 530/380, 381, 403, 387, 808, 809; 128/653, 654; 435/7, 172.2, 240.27; 935/103, 107, 110

[56] References Cited

U.S. PATENT DOCUMENTS

| | | | |
|---|---|---|---|
| 4,036,945 | 7/1977 | Haber | 424/9 |
| 4,454,106 | 6/1984 | Gansow et al. | 424/9 |
| 4,460,559 | 7/1984 | Goldenberg | 424/9 |
| 4,568,544 | 2/1986 | Hasegawa et al. | 424/94.1 |
| 4,634,586 | 1/1987 | Goodwin et al. | 424/9 |
| 4,647,447 | 3/1987 | Gries et al. | 424/4 |
| 4,661,586 | 4/1987 | Levy et al. | 424/85 |

OTHER PUBLICATIONS

Oster et al., Thrombus Radioimmunoscintigraphy: An Approach Using Monoclonal Antiplatelet Antibody, PNAS, 82, 3465-3468, May 1985.

*Primary Examiner*—Esther M. Kepplinger
*Assistant Examiner*—Janelle Graeter
*Attorney, Agent, or Firm*—Berman, Aisenberg & Platt

[57] ABSTRACT

Use of labeled monoclonal antibody 50 H.19 to detect the location and concentration of blood platelets in a host is disclosed. MAb 50 H.19 labeled with a label which can be detected from without the host (e.g. a radiolabel or NMR-label) is intravenously injected to immunoreact with platelets in vivo or is first immunoreacted in vitro with platelets, which are then intravenously injected into the host. By means of the labeled MAb 50 H.19 bound platelets it is possible to detect and locate thrombi, emboli, atherosclerotic obstructions, bacterial endocarditis and to do spleen imaging. In another embodiment of the invention, the MAb 50 H.19 is bound to an enzymatic thrombolytic agent and injected intravenously to permit the therapeutic application of the agent directly to thrombi.

16 Claims, No Drawings

METHOD FOR DETECTING BLOOD PLATELETS

RELATED APPLICATION

This application is a continuation of application Ser. No. 739,697, (now abandoned), filed May 31, 1985, and is also related to application Ser. No. 094,455, filed Sept. 9, 1987, and to application Ser. No. 740,253 (now abandoned), filed June 3, 1985.

SUMMARY OF THE INVENTION

The present invention is directed to a method for detecting blood platelets in a host using a labeled platelet binding antibody. The invention results from the discovery that the monoclonal antibody (MAb) 50 H.19 and fragments thereof react with blood platelets with high affinity and shows little or no binding to other elements in blood.

In accordance with this invention, the antibody is labeled to permit imaging after injection into the host. The labeled antibody can be reacted with platelets in vitro and then injected or the labeled antibody can be injected intravenously, in which case it will react with platelets in vivo. After an elapsed amount of time sufficient for the platelets to pass through the blood stream of the host, the host is scanned to image and detect locations of blood platelets. By observing the location and concentration of platelets, the method of the invention permits location and/or detection of various disorders including lesions of venous thrombosis, bacterial endocarditis, coronary arterial thrombosis, pulmonary emboli and atherosclerosis as well as organ imaging, such as spleen imaging. Because of the high sensitivity of the procedure, a high target-to-background ratio is achieved, thereby obviating the need to utilize background subtraction.

In accordance with another practice of this invention, the antibody is provided with an enzymatic thrombolytic agent and immunoreacted with platelets in vitro or in vivo as described above. The high platelet affinity of the antibody permits the thrombolytic agent to be carried to areas of high platelet concentration, such as thrombi, which is useful in therapy.

The monoclonal antibody 50H.19 is selected by the murine hybridoma S.2.1. (registered with the American Type Culture Collection on May 17, 1985 and assigned the number HB 8807).

DETAILED DESCRIPTION OF THE INVENTION

MAb 50 H.19 which is utilized in the method of the present invention is a biologically pure monoclonal antibody derived from hybridoma ATCC No. HB8807, deposited in the American Tissue Culture Collection. It is purified by known purification techniques, such as the protein-A purification technique. MAb 50 H.19 is more fully described in MacLean et al. (1982) J.N.C.I., 69, No.2, at 357-64, which is incorporated herein by reference.

The present invention relates to the use of the high platelet binding affinity properties of MAb 50 H.19 to detect blood platelets in a host thereby permitting detection of thrombi, emboli, arteriosclerosis and other disorders. MAb 50 H.19 antibody is immunoreactive with blood platelets of human beings as well as other species, e.g. primates and canines. The antibody, or fragment thereof, rapidly reacts with blood platelets and the majority of the bound antibodies remain bound to the platelets for a substantial period. Typically within fifteen minutes of being contacted with blood or blood platelets, no less than forty percent of the antibody is associated with the blood platelets. The bound antibody remains bound for several days. On the other hand, MAb 50 H.19 does not bind to white or red blood cells and relatively little (typically no more than 5%) is found in serum within a very short time after being introduced into the host. Specifically, MAb 50 H.19 and its fragments identified as Fab, Fab', and F(ab')$_2$, as well as mixtures thereof, exhibit this high platelet affinity. References herein to MAb 50 H.19 are to be understood to include MAb 50 H.19 as well as the foregoing platelet specific fragments.

Because MAb 50 H.19 has a high affinity for binding to blood platelets, labeled MAb 50 H.19 can be used to detect the concentration and location of blood platelets in a host when the label is one which can be detected from without the host. For example, radiolabels which can be detected scintigraphically or NMR-labels which can be detected by NMR scanners may be employed. When the labeled MAb 50 H.19 is contacted with the blood platelets of a host, such as a patient believed to be suffering a disorder of the blood vessels, the labeled antibody immunoreacts with the blood platelets. Since the label can be detected from without the patient, it is possible to determine where the host's blood platelets are located and to observe the relative concentrations thereof.

Among the labels suitable for use with MAb 50 H.19 are radiolabels, such as radioactive isotopes of gallium, bromine, technetium, indium, and iodine. Specifically, $Ga^{67}$, $Br^{77}$, $Tc^{99}m$, $In^{111}$, $In^{113}$, $I^{123}$, $I^{125}$, and $I^{131}$ are useful with MAb 50 H.19. The various techniques for radiolabeling are well known to those of ordinary skill in the art and are described in various available references. When radiolabeling with radioactive bromine or iodine, the chloramine-T method first described in Hunter et al. (1962) Nature (London), 194, at 495-96, or the iodogen method first described in Franker & Speck, *Biochem. Biophys. Res. Commun.* 80 at 849-57. or the methods reviewed in Saka, *Radioimmunoimaging and Radioimmunotherapy*, ed. Burchiel & Rhodes (Elsevier: 1983), at 171-84, can be used. For radiolabeling with radioactive technetium, the method described in Crockford et al. U.S. Pat. No. 4,424,200 is recommended, while the bifunctional chelate method described in Wensel & Meares, *Radioimmunoimaging and Radioimmunotherapy*, ed. Burchiel & Rhodes (Elsevier: 1983), at 185-96, is the preferred method when using radioactive gallium or indium.

The presently emerging technology in the field of labeling and imaging is nuclear magnetic resonance (NMR). Useful NMR-labels presently known include gadolinium (Gd) and other cations which will cause a signal shift of NMR. The technique for NMR-labeling suitable for use with MAb 50 H.19 is described in Lauffer, R. B., & Brady, T. J. (1985), "Preparation and Water Relaxation Properties of Proteins Labeled with Paramagnetic Metal Chelates," *Magnetic Resonance Imaging*, 3, at 11-16. As this technology further evolves, additional useful NMR-labels and techniques for NMR-labeling of antibodies will become known, the use of which is contemplated in this invention.

In the practice of the present invention, labeled MAb 50 H.19 is contacted with the blood platelets of a host and the labeled antibody and platelets are allowed to remain in contact for a period of time sufficient to allow the antibody to immunoreact with or bind to the platelets. An amount of labeled antibody sufficient to allow detection of its locations within the host by scanning means must be employed. References to an effective amount of labeled antibody refer to the level of labeled antibody which can be detected by scanning means. Labeled MAb 50 H.19 can be immunoreacted with the blood platelets either in vitro or in vivo. When reacted in vitro, a blood sample of from about one to about ten milliliters is removed from the host. The blood platelets are separated from the blood sample and then immunoreacted with the labeled antibody. The immunoreaction takes place in a physiologically acceptable liquid medium, e.g. dilute human serum albumin. The platelets and the labeled antibody are then allowed to incubate for a period of at least one minute and preferably at least fifteen minutes. The labeled platelets can then be intravenously injected into the host. For reaction in vivo, the labeled antibody may be mixed with a physiologically acceptable liquid carrier and the mixture may be intravenously injected into the host.

For either the labeled platelets from the in vitro reaction or the labeled antibody for in vivo reaction, after intravenous injection, a period of at least about two hours is preferably permitted to elapse prior to scanning the host, although the labeled antibody becomes bound to the platelets in as little as fifteen minutes. The more extended period of time allows the labeled platelets to circulate through the bloodstream and to accumulate at locations of blood platelet concentration.

In cases where a radiolabel is used to label the antibody, the suitable dosages are from about five to about thirty millicuries, and preferably from about ten to about twenty millicuries for a host having a body weight of 70 kg (154 pounds). The typical dosages for direct intravenous injection of the radiolabeled antibody are from about 0.001 to about one milligram per kilogram of body weight, preferably from about 0.001 to about 0.3 mg/kg body weight, and most preferably from about 0.015 to about 0.15 mg/kg body weight.

Because labeled MAb 50 H.19 indicates the location of blood platelets in the host's bloodstream, it is possible to detect a number of disorders by means of labeled MAb 50 H.19. For example, one may detect and locate thrombi by observing where the blood platelets to which the labeled antibody as bound are concentrated. Thus, labeled MAb 50 H.19 is useful in detecting arterial thrombosis and lesions of venous thrombosis. MAb 50 H.19 may also be used for spleen imaging. Further, emboli can be detected and located by observing those locations where the blood platelets exhibit a reduced concentration. Thus, MAb 50 H.19 can be used to detect pulmonary emboli. Atherosclerosis can be detected by observing the size of the blood stream through which the platelets to which the labeled antibody are bound are circulating and thereby detecting where atherosclerotic obstructions are located in the vessels. MAb 50 H.19 can also be used to detect bacterial endocarditis by observing where blood platelets are concentrated in the heart.

Because of its high platelet-specificity and strong binding properties, MAb 50 H.19 is useful in therapy to carry an appropriate agent directly to an area of high blood platelet concentration. For example, MAb 50 H.19 will bind with an enzymatic thrombolytic agent, such as streptokinase, and thence to blood platelets. As the blood platelets are carried through the bloodstream of the host, they will concentrate at thrombi and thereby deliver the thrombolytic agent to the thrombus to be treated.

The following examples are illustrative of the present invention and are not intended to limit the invention.

EXAMPLE I

This example illustrates the platelet-specificity of the 50 H.19 antibody.

A sample of human whole blood was separated by conventional techniques into three factors: (1) platelets, (2) red blood cells, and (3) white blood cells. The three samples were adjusted so that each sample had about the same volume. Radiolabeled MAb 50 H.19 having a radioactivity of 150,000 counts per minute was added to each of the three samples. The samples with the radiolabeled MAb 50 H.19 were incubated for thirty minutes. Following incubation, the samples were spun down and washed with saline. The radioactivity of each of the samples was then measured to determine the amount of binding of the radiolabeled antibody to the cells or platelets. The sample of red blood cells and the sample of white blood cells each showed no significant binding. By contrast the sample of platelets showed between 40% and 50% binding of the total input of labeled MAb 50 H.19.

EXAMPLE II

This example illustrates the utility of labeled MAb 50 H.19 for imaging, detecting, and diagnosing thrombi.

A sample of MAb 50 H.19 radiolabeled with $Tc^{99}m$ was prepared in accordance with the method of Example I of U.S. Pat. No. 4,424,200, which is incorporated herein by reference.

The evaluation of the radiolabeled antibody was performed in adult female mongrel dogs having a body weight of between 20 and 30 kg. Pentobarbital anesthesia was employed and no heparin was used throughout the experiments.

Experimental thrombi were induced by the transcatheter placement of copper coils into the common carotid, pulmonary and femoral arteries, the jugular and femoral veins, and the right ventricle. Thrombi were induced 1, 2, 3, 4, 8 and 48 hours before injection of the radiolabeled antibody. Thrombi were localized in situ by radiography of the copper coils and scintigraphy. Images were obtained 30 minutes after injection with a large field-of-view gamma camera (available from Ohio Nuclear, Solon, Ohio) interfaced to a Gamma-11 system (available from Digital Equipment Corporation, Waltham, Mass.), using a 64×64 matrix. Thrombus-to-background and thrombus-to-blood pool ratios were calculated. At the end of the experiments, the animals were sacrificed by injecting a 12 to 20 mg/kg dose of pentobarbital. In some experiments, the heart and lungs were excised after the death of the animal and analyzed by radiography and scintigraphy before recovering the thrombi, in others, the thrombi, blood and urine and the appropriate ratios calculated.

Venous and arterial thrombi could be consistently visualized as early as 1 to 3 hours after injection. Moreover, focal areas of increased uptake were also observed at sites of intimal damage associated with the experimental protocol, e.g. at sites of catheter entry, even though thrombi could not be identified at these sites at autopsy. Thrombi could also be visualized in segmental pulmonary arteries lying in front of the cardiac blood pool as well as within the right ventricle. No delayed imaging or blood pool subtraction techniques were necessary to identify the thrombi.

The 1, 2, 3, 4, and 8 hour old thrombi could be visualized with this technique. However, the 48 hour old thrombi (shown to be present at autopsy) had the same activity as the background body tissue and thus could not be imaged. Ratios of radioactivity in thrombi to radioactivity in blood were calculated from direct counts and were found to be between 2 to 15. These ratios confirmed the observations made visually on the scintiphotos.

Blood clearance studies were performed in dogs with doses of 0.5 millicuries of the radiolabeled antibody. For blood clearance determinations, samples were obtained at predetermined intervals from one minute to one day after injection. Urine samples of the 0–1, 1–2, 2–3 and 3–4 hour periods were assayed for radioactivity. Results were variously expressed as the percentage of injected activity per whole blood volume (calculated at 7% of body weight) or of injected dose contained in the total urine volume.

Within 3 to 6 minutes after injection, about 50% of the injected activity was cleared from the blood; imaging experiments indicated that the kidney was the major organ removing the activity from the circulation. 18 to 24% of the injected radioactivity was excreted in the urine within 1 to 3 hours. After incubating the radiolabeled antibody with the whole dog blood for 1 hour, 54 to 64% of the activity sedimented with the cellular fraction.

In all 9 dogs studied, no untoward side-effects were observed. Platelet counts before and after the injection of labeled antibody were performed in several dogs and any tendency for increased bleeding was monitored clinically. The doses of the radiolabeled antibody of up to 0.1 mg employed in these studies did not cause any changes in the dogs' platelet counts, nor was there evidence of a hemorrhagic diathesis or other symptoms.

EXAMPLE III

This example illustrates the utility of labeled MAb 50 H.19 for spleen imaging.

A sample of MAb 50 H.19 radiolabeled with $I^{131}$ was prepared by the conventional iodogen method.

Ten human cancer patients were intravenously injected with doses of between one and two milligrams of the radiolabeled antibody, comprising a dose of one millicurie. Serum blood samples were withdrawn from all ten patients at preselected times ranging from fifteen minutes after injection to two weeks after injection. The platelets were separated and the radioactivity measured to determine the percentage of binding of the radiolabeled antibody to the platelets. In all ten patients, the sample taken at fifteen minutes showed no less than 40% binding. The blood samples withdrawn in subsequent days showed no decrease below 40% binding, but rather remained essentially constant. These samples also showed less than 5% free radioactivity in the blood serum.

Imaging showed raw spleen uptake in accordance with the known distribution of labeled platelets in the spleen. No liver uptake occurred except for those patients having metastatic liver cancer. Some tumor uptake was observed for breast tumors, liver tumors, colorectal tumors, and melanomas. Tumor uptake was especially pronounced in those patients having had a splenectomy.

The injection and binding of the radiolabeled antibody had no effect on platelet function and no side effects of any sort were detected in any of the patients.

What is claimed is:

1. A method of detecting blood platelets, comprising:
   (a) contacting blood platelets of a host with an effective amount of labeled monoclonal antibody 50 H.19 which the same as that secreted by hybridoma ATCC HB 8807;
   (b) allowing the labeled antibody to remain in contact with the platelets for a period of time sufficient to allow the antibody to bind to the platelets;
   (c) thereafter detecting the platelets to which the labeled antibody has bound by means capable of detecting the label on the antibody.

2. The method of claim 1 wherein the blood platelets are contacted with the labeled antibody by intravenously injecting the labeled antibody into the bloodstream of the host.

3. The method of claim 1 wherein the blood platelets are isolated from the host prior to being contacted with the antibody in step (a) and are injected into the host after step (b) and prior to step (c).

4. The method of claim 1 wherein the platelets and labeled antibody are allowed to remain in contact for at least fifteen minutes.

5. The method of claim 1 wherein 1 to 2 mg of labeled antibody are contacted with the blood platelets.

6. A method in accordance with claim 1, wherein the antibody is labeled with a radiolabel and step (c) is practiced with a scintigraphic scanner.

7. A method in accordance with claim 6, wherein the radiolabel is selected from the group consisting of $Ga^{67}$, $Br^{77}$, $Tc^{99}m$, $In^{111}$, $In^{113}m$, $I^{123}$, $I^{125}$, and $I^{131}$.

8. A method in accordance with claim 6 wherein from about 0.001 to about 1 mg of labeled antibody/kg of body weight of the host is contacted with the blood platelets.

9. A method in accordance with claim 1 wherein the antibody is labeled with a cation which will cause a signal shift of NMR and step (c) is practiced with an NMR scanner.

10. A method in accordance with claim 9 wherein Gd-labeled antibody is used.

11. A method in accordance with claim 1 wherein thrombi are detected by observing where the blood platelets to which labeled antibody has bound are concentrated.

12. A method in accordance with claim 1 wherein step (c) is practiced to image the spleen of the host.

13. The method in accordance with claim 1 further comprising detecting and locating emboli by observing those locations where the blood platelets to which the labeled antibody is bound exhibit a reduced concentration.

14. The method in accordance with claim 1 further comprising detecting atherosclerosis by observing the size of the blood stream in which the platelets to which the labeled antibody is bound are circulating and thereby detecting where atherosclerotic obstructions are located in the blood vessels.

15. The method in accordance with claim 1 further comprising the detection of bacterial endocarditis by observing where blood platelets to which labeled antibody has bound are concentrated in the heart.

16. A method of delivering a thrombolytic agent to a thrombus in a host comprising:
   (a) attaching a thrombolytic agent to monoclonal antibody 50 H.19, which is the same as that secreted by hybridoma ATCC HB 8807, and
   (b) introducing the antibody with the attached thrombolytic agent into the bloodstream of the host.

* * * * *

UNITED STATES PATENT AND TRADEMARK OFFICE
CERTIFICATE OF CORRECTION

PATENT NO. : 4,990,326

DATED : February 5, 1991

INVENTOR(S) : Antoine A. Noujaim, Sherwood Park, Bryan M. Longenecker, Buck A. Rhodes, Paul O. Zamora It is certified that error appears in the above-identified patent and that said Letters Patent is hereby corrected as shown below:

On the title page, item [75], "Antoine A. Noujaim, Sherwood Park...both of Canada" should read --Antoine A. Noujaim, Sherwood Park, Alberta; Bryan M. Longenecker, Edmonton, Alberta, both of Canada; Buck A. Rhodes, Albuquerque, New Mexico; Paul O. Zamora, Albuquerque, New Mexico.
Column 1, line 44, "selected" should read --secreted--. Claim 1, line 4, "which" should read --which is--.

Signed and Sealed this

Fifteenth Day of September, 1992

Attest:

DOUGLAS B. COMER

*Attesting Officer*  *Acting Commissioner of Patents and Trademarks*